United States Patent
Neuhaus et al.

(10) Patent No.: US 11,484,683 B2
(45) Date of Patent: Nov. 1, 2022

(54) PATIENT VALVE FOR VENTILATING A PATIENT WITH A VENTILATOR

(71) Applicant: WEINMANN EMERGENCY MEDICAL TECHNOLOGY GMBH + CO. KG, Hamburg (DE)

(72) Inventors: Christian Neuhaus, Hamburg (DE); Matthias Pulla, Hamburg (DE); Johannes Kreuzer, Hamburg (DE); Samir El Diwany, Norderstedt (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 433 days.

(21) Appl. No.: 16/605,403

(22) PCT Filed: Feb. 16, 2018

(86) PCT No.: PCT/DE2018/000041
§ 371 (c)(1),
(2) Date: Oct. 15, 2019

(87) PCT Pub. No.: WO2018/196895
PCT Pub. Date: Nov. 1, 2018

(65) Prior Publication Data
US 2020/0038619 A1 Feb. 6, 2020

(30) Foreign Application Priority Data

Apr. 27, 2017 (DE) .................... 10 2017 004 137.7
Nov. 10, 2017 (DE) .................... 10 2017 010 485.9

(51) Int. Cl.
*A61M 16/20* (2006.01)
*A61M 16/08* (2006.01)
*A61M 16/10* (2006.01)

(52) U.S. Cl.
CPC ...... *A61M 16/208* (2013.01); *A61M 16/0833* (2014.02); *A61M 16/0858* (2014.02);
(Continued)

(58) Field of Classification Search
CPC .. A61M 16/00; A61M 16/08; A61M 16/0808; A61M 16/0833; A61M 16/0841;
(Continued)

(56) References Cited

U.S. PATENT DOCUMENTS 2,834,339 A    5/1958 Vivian
2,841,142 A * 7/1958 Hay .................... A61M 16/201
                                                                 128/205.13
(Continued)

FOREIGN PATENT DOCUMENTS

DE      10035938 A1 * 2/2001 ........ A61M 16/0858
DE      10035938 A1    2/2001
(Continued)

OTHER PUBLICATIONS

English language machine translation of DE-102008026321-A1.*
English language machine translation of WO-2009089807-A1.*
English language machine translation of WO-2017059667-A1.*

*Primary Examiner* — Joseph D. Boecker
(74) *Attorney, Agent, or Firm* — Lucas & Mercanti, LLP; Klaus P. Stoffel

(57) ABSTRACT

A patient valve for ventilating a patient with a ventilator, including a first valve element having at least one connection, wherein the at least one connection is oriented with the central axis thereof at an angle deviating from the vertical position in relation to the patient valve central axis, such that a shortened patient valve having a reduced dead space volume is supported.

17 Claims, 3 Drawing Sheets

(52) U.S. Cl.
CPC ...... *A61M 16/1005* (2014.02); *A61M 16/206* (2014.02); *A61M 16/209* (2014.02); *A61M 16/085* (2014.02)

(58) Field of Classification Search
CPC ............ A61M 16/085; A61M 16/0858; A61M 16/1005; A61M 16/20; A61M 16/201; A61M 16/206; A61M 16/208; A61M 16/209; A62B 9/02; A62B 9/022; A62B 18/10
See application file for complete search history.

(56) References Cited

U.S. PATENT DOCUMENTS

| | | |
|---|---|---|
| 3,063,620 A | 11/1962 | Geoffrey |
| 10,987,482 B1 * | 4/2021 | Duis .................. A61M 16/208 |
| 2008/0092898 A1 | 4/2008 | Schneider et al. |
| 2014/0121607 A1 * | 5/2014 | Chang ............... A61M 16/0833 604/246 |
| 2015/0231028 A1 * | 8/2015 | Belalcazar ............ A61M 16/20 601/43 |

FOREIGN PATENT DOCUMENTS

| | | | |
|---|---|---|---|
| DE | 102008026321 A1 * | 12/2008 | ........ A61M 16/0858 |
| DE | 102008026321 A1 | 12/2008 | |
| DE | 202015100434 U1 | 3/2015 | |
| EP | 2359889 A1 | 8/2011 | |
| GB | 1602925 A | 11/1981 | |
| WO | 0045883 A1 | 8/2000 | |
| WO | 0166175 A1 | 9/2001 | |
| WO | 2009089807 A1 | 7/2009 | |
| WO | WO-2009089807 A1 * | 7/2009 | ............ A61M 16/06 |
| WO | 2010061173 A1 | 6/2010 | |
| WO | WO-2017059667 A1 * | 4/2017 | .......... A61M 16/206 |

* cited by examiner

PATIENT VALVE FOR VENTILATING A PATIENT WITH A VENTILATOR

CROSS-REFERENCE TO RELATED APPLICATIONS

The present application is a 371 of International application PCT/DE2018/000041, filed Feb. 16, 2018, which claims priority of DE 10 2017 004 137.7, filed Apr. 27, 2017, and DE 10 2017 010 485.9, filed Nov. 10, 2017, the priority of these applications is hereby claimed and these applications are incorporated herein by reference.

BACKGROUND OF THE INVENTION

The invention relates to a patient valve for ventilating a patient with a ventilator, having a first valve element with at least one port.

In modern medicine, a wide variety of medicaments are used in many different situations in order to alleviate or eliminate acute and chronic symptoms caused by diseases, harmful external influences and accident-related injuries. In emergency situations too, medicaments are used in order, for example, to prevent imminent failure of the vital functions of a victim of an accident or to prevent disease-related collapse of individuals.

In emergency situations, particularly in the initial pre-hospital care of patients, it is often necessary to administer oxygen by emergency ventilation. To be able to deliver this oxygen-enriched respiratory air to the patient in situ, it is customary for mobile and possibly also portable ventilators, which generally operate pneumatically, to be carried for example in ambulances or first-response vehicles, in order to be available at the site of an emergency.

One variant of the ventilation technique dispenses with the oxygen enrichment of the respiratory air. In these cases, a patient's breathing is supported by the delivery of respiratory air at a slight overpressure in relation to the atmosphere. Both variants, i.e. with or without oxygen enrichment, are designated as non-invasive ventilation by means of positive pressure. It is likewise possible to ventilate invasively, for example by intubation.

The devices for non-invasive ventilation by means of positive pressure are primarily formed by the actual ventilators and by the connection systems between the ventilator and the patient who is to be ventilated. The connection system has at least a respiratory air guide, in most cases formed by a hose and by a contact interface, or an interface in the form of a breathing mask (nose mask, nose/mouth mask, face mask) or a breathing helmet. The connection system can be supplemented by a so-called patient valve which, depending on requirements, combines one or more functions. In particular, the patient valve can be configured as a directional valve.

In ventilation techniques, and in particular in emergency ventilation, it is important that the connection systems and/or contact interfaces to the patient's airways are as light as possible, slim and with reduced dead space.

Dead space (or also respiratory space) is understood, in the narrower sense of breathing masks, as the interspace between the mask and the patient's face. This means that the dead space of the inner mask is limited or minimized. The person wearing the breathing mask exhales into this. The dead space must be as small as possible, since otherwise a large part of the exhaled air containing carbon dioxide remains there and, with all its damaging consequences, is re-inhaled.

The dead space can be negatively influenced, that is to say enlarged, by the patient valve arranged directly downstream from the breathing mask. In light of this and depending on the design and structure, the avoidable volume of the connection system carrying respiratory air can enlarge the dead space in an undesired manner.

Furthermore, if connection systems and/or contact interfaces to the patient's airways are as light as possible, slim and have a reduced dead space, the risk of undesired and possibly life-threatening extubation, that is to say the removal of the connection system or loss of contact between the interface and the patient, is reduced.

Furthermore, if connection systems and/or contact interfaces are light, slim and have a reduced dead space, they support the ventilation of smaller patients, in particular children, and make the work of the user easier.

In addition, connection systems, interfaces and patient valves should be able to be used for different ventilators with different ports, for example varying nominal widths or auxiliary functions. It is important among other things that the components to be attached, for example hoses, cables, measurement appliances, control appliances, etc., are attached in the correct way and without being mixed up. Safe attachment of the required hoses must also be ensured.

SUMMARY OF THE INVENTION

The object of the invention is to further develop the existing patient valves, as components of the connection systems between the ventilator and the patient who is to be ventilated, and to at least partially reduce the aforementioned disadvantages.

The teaching according to the invention proposes a patient valve as a component of the connection system, which patient valve supports the modularity of the connection system and in this way can be used for different ventilators and/or patients. A compact structure results in the smallest possible dead space, and the light and slim design is permitted by the attachments being directed away toward the ventilation hose. The attachments are designed to be error-proof and/or so that they cannot be mixed up, and the individual connections do not have to be adhesively bonded. An optional valve adapter is designed so as to be exchangeable.

The new kind of patient valve is at least in one part and is preferably designed as an exhalation valve for ventilators, breathing bags and/or emergency ventilators. The at least one port of the patient valve is of an angled configuration, that is to say is at an angle deviating from the vertical in relation to the patient valve central axis.

By virtue of the structure according to the invention, the patient valve can be made shorter and in this way supports the reduction of dead space. The invention recognizes that an angle range of ca. 25 degrees to ca. 75 degrees, and in particular an angle range of ca. 30 degrees to ca. 50 degrees, between port central axis and patient valve central axis supports the shortening of the structure.

Based on a further inventive concept, the compactness of the patient valve can support a reduction of dead space: If two or more ports are provided, then, alternatively or additionally to being at an angle, they can be positioned deviating from an arrangement aligned in the longitudinal direction. This can be achieved, for example, by a positioning in the circumferential direction at approximately the same height and at an offset angle to each other.

A risk of error or mix-up, that is to say of incorrect assignment of hoses, cables, measurement appliances, control appliances, etc., to the respective port, is counteracted by suitable geometries and/or dimensions.

If the patient valve is in two parts, provision is made according to the invention for the attachment between the parts of the patient valve to be of a conical configuration and to be safe from being confused with standard ventilation cones. Customary ventilation cone dimensions are 22 mm and/or 15 mm. The attachment between the parts of the patient valve is always the same, and in this way any desired combinations with functionally different components can be made available.

In order to additionally or alternatively support a modularity of the connection system and to ensure the compatibility with different interfaces, the patient's airways are attached via standard cones from ventilation technology, that is to say with a 15 mm or 22 mm inside dimension.

In an illustrative embodiment of the patient valve, a variant with an integrated pressure tap for ventilation control is provided, which permits an attachment of the exhalation membrane to the ventilation hose via a defined throttle.

A further variant of the patient valve can have at least one port for supply of oxygen into the ventilation hose, for example in order to buffer the latter.

The patient valve can optionally have at least one port for pressure measurement, for example for measuring the airway pressure of the patient.

Alternatively or additionally, the patient valve can have at least one port for suction of exhalation gases for gas analysis. The same applies to control lines of various types.

Each of the ports according to the invention can be configured with or without a check function, for example realized via a membrane or a directional valve.

The outlet of the patient valve in the direction of the ventilation hose can also be configured as a blind plug, such that the exhalation air is conveyed into the environment. The inhalation air is not typically delivered through the valve. The valve preferably serves only to discharge the exhaled air.

Likewise, provision can optionally be made that the patient valve is designed to be disposed of after a single use.

A further variant of the invention can be realized by arranging an optional check membrane in the patient valve channel carrying respiratory air. The check membrane, which performs the function of a directional valve, ensures that rebreathing into the ventilation hose is prevented.

BRIEF DESCRIPTION OF THE DRAWING

Illustrative embodiments of the invention are depicted in the drawings, in which.

DETAILED DESCRIPTION OF THE INVENTION

Figure 1:
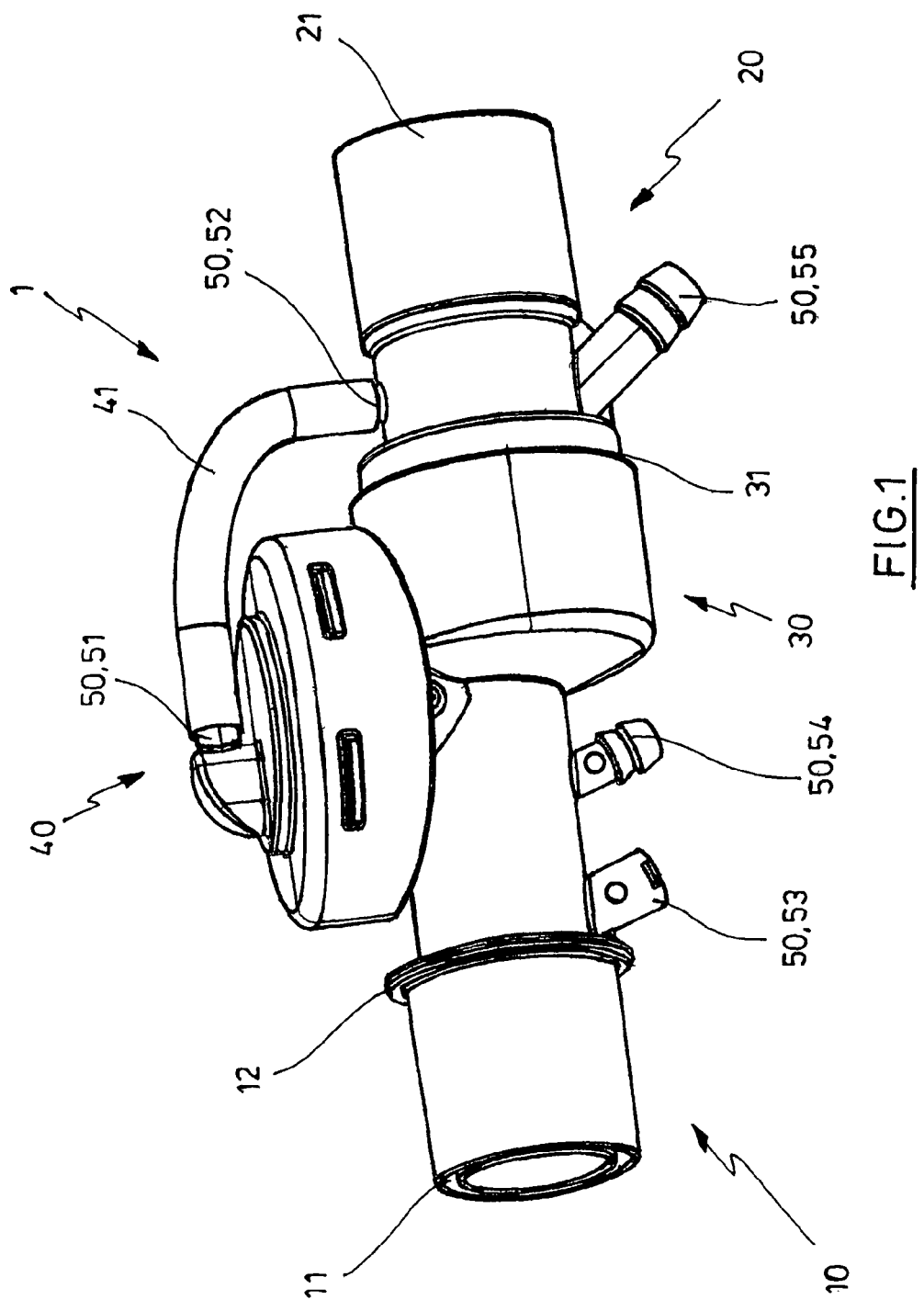
FIG. 1 shows a first possible embodiment of the patient valve (1) according to the invention, with pressure regulation port (50, 51) connected to integrated pressure tap (50, 52) and oxygen supply (50, 55)

FIG. 1 shows a three-dimensional view of a first possible embodiment of the patient valve (1) according to the invention in a multi-part variant. The patient valve (1) is configured here as an exhalation valve and is formed by a first valve element (10) and a second valve element (20) in combination with a pressure control element (40). The pressure control element (40) is an integral component part of the first valve element (10), such that the example of the patient valve (1) in this variant is in two parts and is configured with a connection site (30). One-part and/or at least three-part embodiments are also possible.

The pressure control element (40) is here configured with a pressure regulation port (50, 51), which is operatively connected via a control line (41) to an integrated pressure tap (50, 52), with which the second valve element (20) is provided in this variant.

In this example of a patient valve (1), a variant of the second valve element (20) is used that has an oxygen supply (50, 55). The attachment of a breathing hose and/or of a blind plug is assisted by the attachment piece (21) provided.

The one-piece combination, shown in FIG. 1, of the first valve element (10) with the pressure control element (40) is coupled to the second valve element (20) via a connection site (30). The connection site (30) with its partition plane (31) is configured in such a way that, instead of the second valve element (20), it is possible for different second valve elements (20) or a blind plug to be coupled in modular fashion.

The one-piece illustrative embodiment of the first valve element (10) with pressure control element (40) has at least one port (50) of angled shape, that is to say at an angle deviating from the vertical in relation to the patient valve central axis. By virtue of the design according to the invention, the patient valve can be shorter and in this way supports the reduction of dead space. Ports (50) can be provided as $CO_2$ measurement port (53) and/or as airway pressure measurement port (54).

The first valve element (10) generally has an airway attachment region (11), which is often conically shaped, and also a collar (12), which serves as an axial bearing shoulder for an interface, a hose or a sleeve.

Figure 2:
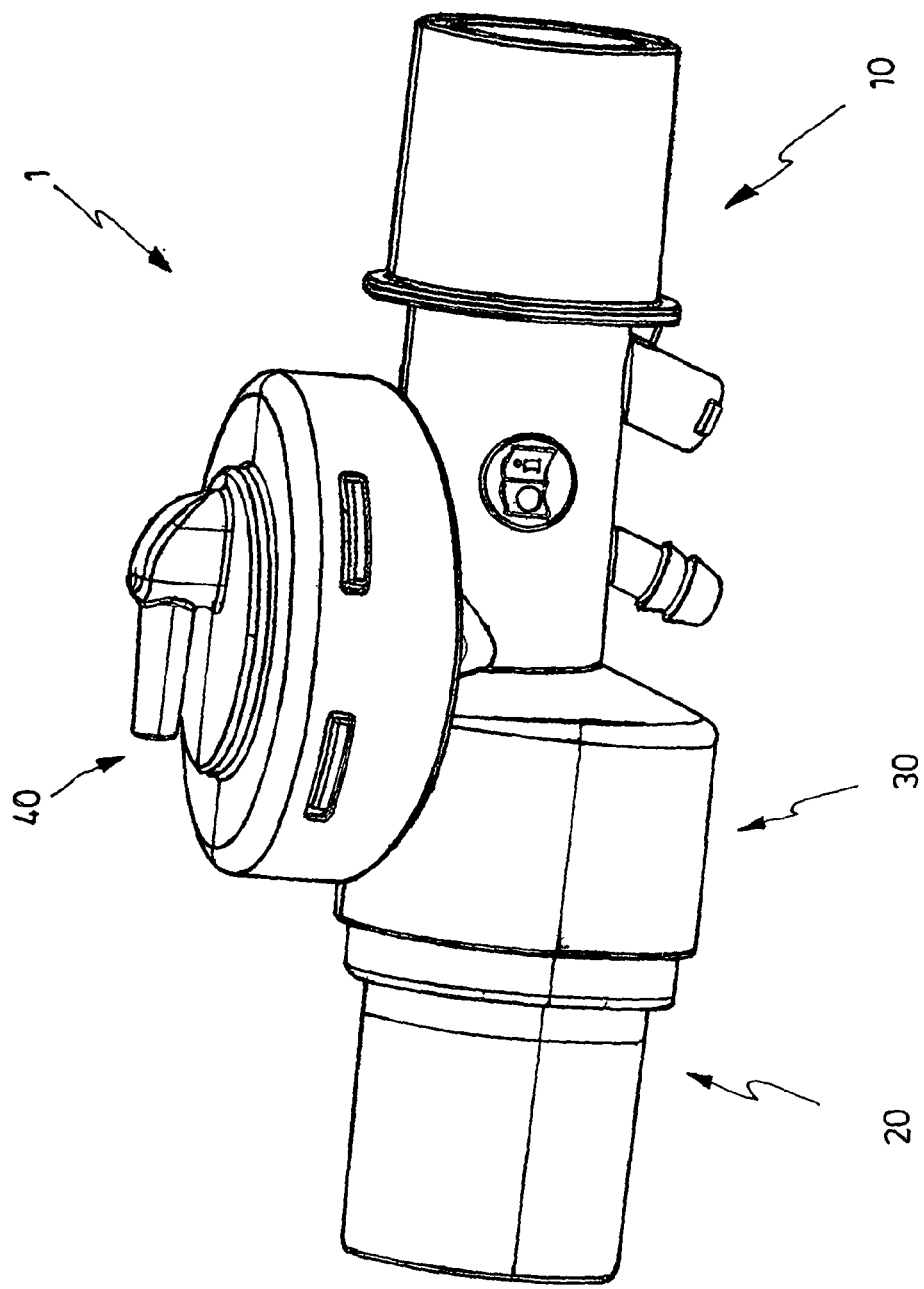
FIG. 2 shows a further possible variant of the patient valve (1) according to the invention, with pressure regulation port (50, 51) and without oxygen supply (50, 55) and also without integrated pressure tap (50, 52)

FIG. 2 shows a perspective view of a further possible variant of the patient valve (1) according to the invention, with pressure regulation port (50, 51) and without oxygen supply and also without integrated pressure tap. This variant illustrates the possible modularity of differently configured first and/or second valve elements (10, 20), by means of the connection site (30) adapted to different variants.

Figure 3:
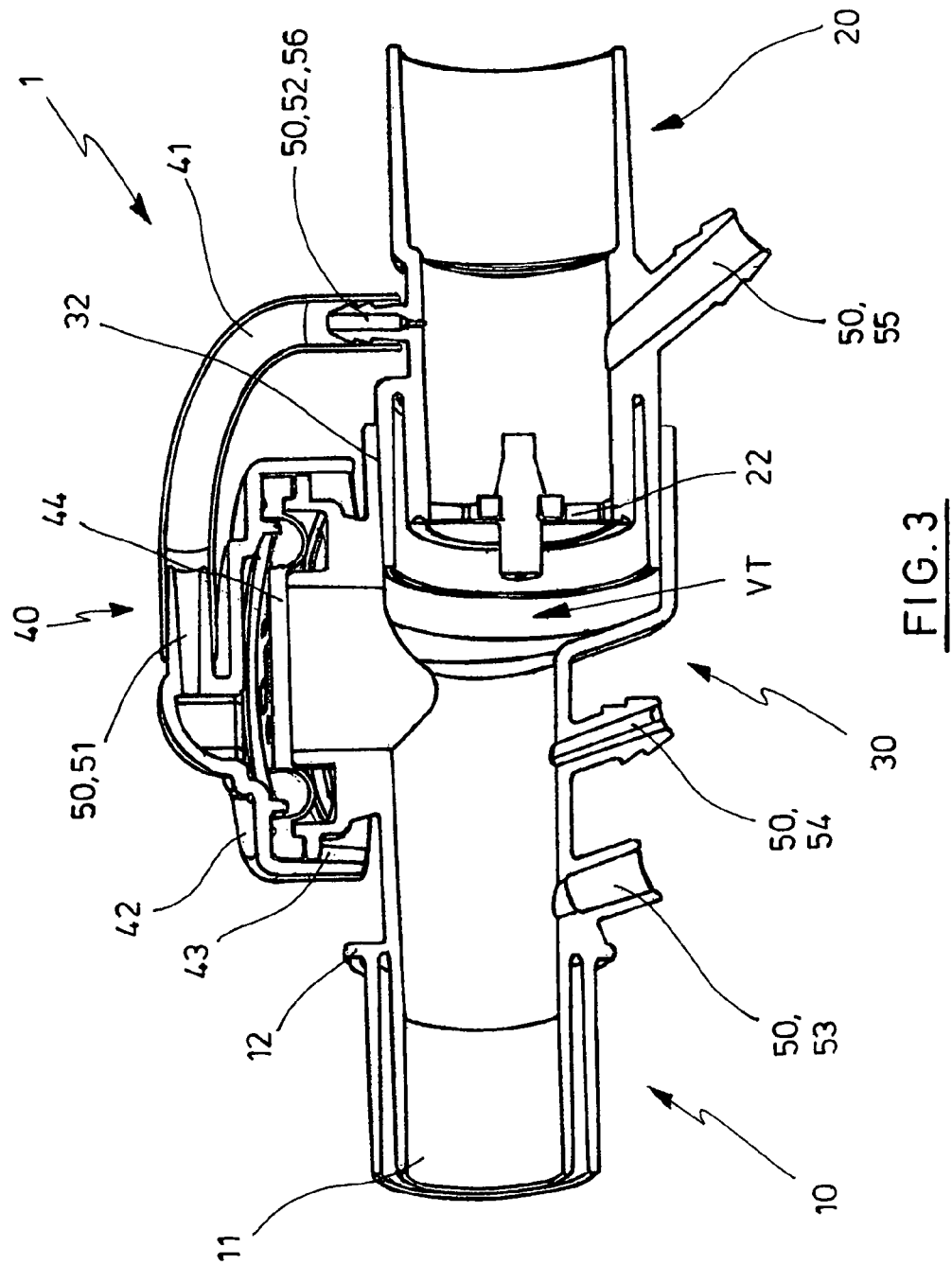
FIG. 3 shows the sectional view of the patient valve (1) according to the invention from FIG. 1, with pressure regulation port (50, 51) connected to integrated pressure tap (50, 52) and oxygen supply (50, 55).

FIG. 3 comprises the three-dimensional sectional view of the patient valve (1) according to the invention from FIG. 1, with pressure regulation port (50, 51) connected to integrated pressure tap (50, 52) and oxygen supply (50, 55). This variant of the patient valve (1) is designed as an exhalation valve and has a pressure control element (40), which is equipped with a control membrane (44). At the airway side, the control membrane (44) is acted upon by the respiratory pressure or the exhalation pressure. At the control side, the control pressure applies via the control pressure outlet (52) and the control line (41) and the control inlet (51). Optionally, and as shown in this example, a throttle (56) can be provided in the control outlet (52).

The control membrane (44) can be configured as a PEEP membrane or can be realized functionally as such, so that the lowest pressure value of a respiratory cycle at the end of the expiration in the lung constitutes the control basis. PEEP stands for positive end expiratory pressure.

The pressure control element (40), configured as a housing around the control membrane (44), has a cover (42), which is coupled by a snap-fit connection (43) and is configured to be secure against rotation, in order to simplify assembly and prevent incorrect fitting.

The illustrative embodiment shown in FIG. 3 has, in the second valve element (20), a check membrane (22) which prevents rebreathing into the ventilation hose or into the second valve element (20). The check membrane (22) is positioned axially at the front end in the second valve element (20), in such a way that the dead space volume (VT) that forms is at least reduced. In this way, a reduction of dead space is obtained that is in addition to the dead space reduction obtained through the reduced length of the patient valve (1) by virtue of the geometric configuration of the at least one port (50) in an angled shape.

In order to prevent incorrect fitting, the connection site (30) of this illustrative embodiment is configured as an error-proofing cone (32). In order to couple the two valve elements (10, 20), in the first step the connection is produced at the connection site (30) by pushing said valve elements axially one into the other, and, in the second step, the control line (41) is connected to the ports (51, 52).

The invention claimed is:

1. A patient valve for ventilating a patient with a ventilator, comprising: a first valve element with at least two ports, each port having a central axis; and a pressure control element having a control membrane, wherein each port is oriented so that each port central axis is at an angle deviating from a perpendicular position in relation to a central axis of the patient valve so that a dead space volume of the patient valve is delimited, wherein the at least two ports include a first port that is a $CO_2$ port and a further port that is an airway pressure measurement port, and wherein the at least two ports are arranged on a lower side of the first valve element directed in a vertical direction downwards, wherein the at least two ports further include an oxygen supply port.

2. The patient valve according to claim 1, wherein the angle is in an angle range of about 25 degrees to about 75 degrees between each port central axis and the patient valve central axis.

3. The patient valve according to claim 2, wherein the angle is in an angle range of about 30 degrees to about 50 degrees between each port central axis and the patient valve central axis.

4. The patient valve according to claim 1, wherein the at least two ports are in alignment in a longitudinal direction of the patient valve.

5. The patient valve according to claim 1, wherein the pressure control element is mounted to the first valve element.

6. The patient valve according to claim 5, wherein the pressure control element has a cover that is coupled by a snap-fit connection and is configured to be secure against rotation.

7. The patient valve according to claim 1, wherein the control membrane is a PEEP control membrane.

8. The patient valve according to claim 1, further comprising a control inlet port via which pressure is applicable to the control membrane.

9. The patient valve according to claim 8, further comprising a second valve element, wherein the first valve element is couplable to the second valve element at a connection site.

10. The patient valve according to claim 9, wherein the connection site has a partition plane.

11. The patient valve according to claim 9, wherein the connection site is configured as a cone.

12. The patient valve according to claim 9, wherein the second valve element has a control port, the control inlet port of the pressure control element being operatively connectable to the control port so that pressure is appliable to the control membrane.

13. The patient valve according to claim 12, further comprising a control line that provides the operative connection.

14. The patient valve according to claim 9, wherein the second valve element has an oxygen supply port so that oxygen is introducable in any desired concentrated form into the second valve element.

15. The patient valve according to claim 9, wherein the second valve element has a check membrane axially positioned at a front end in the second valve element so as to limit the dead space volume.

16. The patient valve according to claim 1, wherein the patient valve is configured as a disposable, single-use valve.

17. The patient valve according to claim 1, wherein the patient valve is an exhalation valve.

* * * * *